United States Patent [19]

Keating

[11] 3,993,651
[45] Nov. 23, 1976

[54] TRIETHYLENEDIAMINE RECOVERY

[75] Inventor: Kenneth Patrick Keating, Austin, Tex.

[73] Assignee: Texaco Development Corporation, New York, N.Y.

[22] Filed: Mar. 17, 1975

[21] Appl. No.: 558,769

[52] U.S. Cl. .............................................. 260/268 T
[51] Int. Cl.$^2$ ..................................... C07D 471/08
[58] Field of Search .............................. 260/268 T

[56] References Cited
UNITED STATES PATENTS

| | | | |
|---|---|---|---|
| 2,950,282 | 8/1960 | Farkas | 260/268 T |
| 3,045,018 | 7/1962 | Mascioli | 260/268 T |
| 3,120,525 | 2/1964 | Muhlbauer et al. | 260/268 T |

OTHER PUBLICATIONS

Houdry Process Corp., Chemical Abstracts, vol. 58, p. 8903d, (1963).

Primary Examiner—Nicholas S. Rizzo
Assistant Examiner—Jose Tovar
Attorney, Agent, or Firm—James L. Bailey; Lee G. Meyer

[57] ABSTRACT

A process is provided for recovering substantially pure triethylenediamine in liquid propylene glycol solutions directly from a crude triethylenediamine reaction mixture without the need to purify the triethylenediamine by crystallization. The process includes initially admixing propylene glycol with a crude triethylenediamine liquid reaction product mixture. The admixture thus formed is then distilled under conditions such that the triethylenediamine and propylene glycol codistill. The codistillate is then collected as the substantially pure triethylenediamine solute in liquid propylene glycol solution. The collected codistillate being substantially free of reaction by-products can be used directly to catalyze urethane systems.

12 Claims, No Drawings

3,993,651

TRIETHYLENEDIAMINE RECOVERY

BACKGROUND OF THE INVENTION

1. Field of the Invention

This invention relates to the recovery of substantially pure triethylenediamine; and, more particularly to a process for recovering a triethylenediamine solute in liquid propylene glycol solutions directly from crude triethylenediamine reaction product mixtures.

2. Prior Art

Triethylenediamine (TEDA) is a valuable commercial product, particularly as an accelerator or catalyst in conventional urethane systems employing a wide variety of isocyanates and polyols as reactants. Several methods for preparing triethylenediamine are well known. For example, one process is described by O. Hromatka et al. in Berichter, Vol. 76, pages 712–717 (1943), wherein triethylenediamine is obtained by the process of heating the dihydrochloride of N-(2-hydroxyethyl)piperazine. Another process involves the gaseous phase cyclization of N-hydroxyethyl piperazine vapor in the presence of a solid acid catalyst. Another well-known process is described in U.S. Pat. No. 3,080,371 to Spielberger et al which includes the liquid phase process of heating N-(2-hydroxyethyl)piperazine in the presence of a mono- or dicarboxylic acid catalyst at a temperature of about 230°–350° C.

Generally, such known processes result in the formation of crude reaction product mixtures containing the triethylenediamine, water, by-products such as piperazine and high molecular weight polymers, catalysts and solvents, if any are employed. Triethylenediamine is normally separated from the crude reaction product by fractional distillation followed by one or more crystallization steps. The substantially pure solid triethylenediamine thus recovered is then dissolved in a suitable solvent for use as a urethane catalyst.

These generally described conventional techniques for recovering triethylenediamine have several disadvantages. Pure triethylenediamine has a freezing point of 159.8° C and a boiling point of 174° C. Pure triethylenediamine thus is normally a liquid over a very narrow temperature range of 14.2° C. In view of this fact it is extremely difficult to separate triethylenediamine from its crude reaction product mixtures by conventional techniques other than crystallization. For example, pure triethylenediamine cannot be readily separated from reaction mixtures by conventional distillation techniques. Further, triethylenediamine readily freezes in the distillation equipment including condensation apparatus, vent lines, and the like, causing equipment blockage problems. Solid, e.g., crystallized, triethylenediamine is also difficult to work with. For example, the crystalline material tends to hydrate. Further, the solid compound is toxic requiring the use of special handling equipment to minimize human exposure.

In as much as conventional urethane systems normally utilize liquid reaction components and the solid triethylenediamine is difficult to handle, store, and ship, the solid is normally dissolved in a suitable solvent, e.g., dipropylene glycol which is compatible with urethane systems. These triethylenediamine solutions have heretofore been prepared by initially obtaining a substantially pure solid triethylenediamine by the methods previously described herein and then dissolving the solid in a suitable solvent.

In the present invention, substantially pure triethylenediamine is recovered directly from the crude reaction product mixture without the need for crystallization. The substantially pure triethylenediamine is recovered in a liquid solution which is substantially free from reaction by-products and can be used directly as a catalyst in urethane systems. Triethylenediamine liquid solutions thus obtained negate the necessity of handling solid triethylenediamine.

SUMMARY OF THE INVENTION

In accordance with the broader aspects of the invention, propylene glycol is admixed with a crude triethylenediamine reaction product mixture. The resultant admixture is distilled under conditions such that the propylene glycol and the triethylenediamine form a substantially pure codistillate which is thereafter collected as the substantially pure triethylenediamine propylene glycol liquid solution.

In a preferred embodiment a crude aqueous triethylenediamine liquid reaction mixture is obtained by heating N-hydroxyethyl piperazine in the presence of a carboxylic acid to temperatures of about 240°–270° C and adding water to the crude reaction effluent obtained therefrom. Propylene glycol is then admixed with the crude aqueous mixture. The resultant admixture is fractionally distilled to provide a propylene glycol-TEDA codistillate collected at head temperatures of from about 184° to about 195° C at atmospheric pressures. The codistillate is liquefied by condensation.

DETAILED DESCRIPTION OF PREFERRED EMBODIMENT

According to a preferred process, substantially pure triethylenediamine (TEDA) is recovered directly from a crude aqueous triethylenediamine liquid reaction mixture as a solute in liquid propylene glycol solution. The liquid solution can thereafter be used directly to catalyze urethane systems.

Preferably the crude triethylenediamine reaction effluent is obtained by initially charging a heated reaction kettle fitted with agitation apparatus and a distillation column with N-(2-hydroxyethyl)piperazine (HEP) and carboxylic acid catalyst. The liquid phase reaction is carried out by well known methods, for example those disclosed in U.S. Pat. No. 3,080,371.

The crude triethylenediamine reaction effluent thus obtained is collected in an appropriate vessel and sufficient water is added thereto to produce a crude aqueous liquid TEDA reaction mixture containing from 45–55 wt. % water. To the aqueous mixture is added propylene glycol in an amount sufficient to provide a collected codistilled solution which contains about 33% by weight to about 37% by weight TEDA.

The admixture of propylene glycol and crude aqueous reaction product is then distilled by employing conventional distillation techniques and equipment. Preferably the distillation is carried out continuously by employing a plurality of distillation columns but can be carried out as, for example, a batchwise or semicontinuous process. During the distillation, the lower boiling point materials such as water, piperazine, and other by-products are initially collected by taking them overhead at distillation head temperatures of up to about 184° C at atmospheric pressure.

The propylene glycol and triethylenediamine codistillate is collected overhead at head temperatures within the range of from about 184° C to about 195° C at atmospheric pressure. The codistillate fraction is then collected, by conventional condensation methods. This can be accomplished without encountering TEDA freezing problems.

The triethylenediamine solution thus prepared contains substantially pure triethylenediamine which is present substantially as a solute of the solution. The triethylenediamine solution is substantially free of reaction by-product and can be used directly to catalyze urethane systems. The triethylenediamine thus recovered is not in the crystalline or solid form thus substantially reducing the problems of handling, toxicity, and shipping previously encountered.

Propylene glycol is nondeleterious to conventional urethane systems and has a boiling point of 187° C which is substantially close to the boiling point of triethylenediamine. Propylene glycol will readily codistill with triethylenediamine by employment of conventional batch-type and continuous distillation techniques to form an essentially pure solution of triethylenediamine and propylene glycol. Moreover, triethylenediamine and propylene glycol solutions have been found to be quite stable during storage.

In addition, the solutions of triethylenediamine and propylene glycol that can be prepared by the process of the present invention have lower freezing points for any given concentration of triethylenediamine in solution than most commercially available triethylenediamine-glycol compound solutions. These commercial solutions usually consist of triethylendiamine dissolved in dipropylene glycol. For example, a commercial solution of triethylenediamine dissolved in dipropylene glycol having 33 wt. % triethylenediamine (DABCO 33-LV, Air Products and Chemicals, Houdry Division, 1337 Chestnut Street, Philadelphia, Pa. 19107) freezes at a temperature of about 0° C. By comparison, a 33 wt. % solution of triethylenediamine dissolved in propylene glycol prepared in accordance with the present invention has a freezing point of about −23° C.

In carrying out the process of the invention, water is preferably added to the crude triethylenediamine effluent to produce a crude aqueous liquid triethylenediamine reaction product mixture. The addition of the water is not critical to carrying out the process of the instant invention, but is added primarily as a diluent and/or solvent. Since TEDA is soluble in water, the aqueous crude reaction product mixture is more easily handled and transferred at lower temperatures without encountering freezing or precipitation of the dissolved TEDA.

The amount of water added to the crude triethylenediamine effluent is somewhat empirical and will depend upon the handling and transfer temperatures desired as well as the concentration of triethylenediamine present. Preferably, water is added in an amount sufficient to attain an aqueous crude reaction product mixture containing about 45 to 55 wt. % water.

The propylene glycol is added to the crude triethylenediamine reaction product mixture in an amount sufficient to codistill substantially all of the triethylenediamine present without encountering freezing problems. Preferably, the propylene glycol is added in an amount sufficient to provide a collected codistilled solution having a triethylenediamine concentration of at least about 33 wt. % up to about 37 wt. %. This range is preferred inasmuch as triethylenediamine-glycol compound solutions are usually marketed commercially in 33 wt. % concentrations.

The specific amount of propylene glycol which may be added to a given crude triethylenediamine reaction product mixture is primarily dependent upon the amount of triethylenediamine present. Thus, the amount required to codistill substantially all of the triethylenediamine present can be readily determined by those having ordinary skill in the art without undue experimentation.

The admixture of propylene glycol and crude triethylenediamine reaction product may then be distilled employing any of the well-known conventional distillation techniques and equipment.

The process of the invention can be employed to recover substantially pure triethylenediamine solutions directly from crude triethylenediamine reaction product mixtures obtained by practically any known liquid phase process for the preparation of triethylenediamine.

The codistillation step can be carried out at superatmospheric or subatmospheric pressures if desired. Such techniques and temperatures required are well-known to those skilled in the art and can be readily determined without undue experimentation. Fractional distillation columns may be utilized with very narrow head temperature ranges to reduce, for example, the amount of piperazine present in the collected crude reaction product mixture. Excess water can be removed from the admixture of propylene glycol and aqueous TEDA reaction product mixture by, for example, azeotropic distillation techniques. Such a technique can include the initial addition of a lower boiling point nondeleterious hydrocarbon to the crude reaction product mixture.

The process of the instant invention may be employed to recover TEDA solutions from the crude liquefied reaction product mixture of known vapor phase preparation procedures. However, most vapor phase procedures for producing triethylenediamine form by-products which have a boiling point in a range such that codistillation in accordance with the present invention may not produce a TEDA solution free of by-products. Therefore, in order to practice the instant invention, the vapor phase reaction products could require a removal of these similar boiling impurities, prior to the addition of the propylene glycol.

The process of the invention is further disclosed in the following examples, which are illustrative but not limitative thereof.

In the following examples the crude triethylenediamine reaction product mixture employed was prepared substantially by the process of heating N-(2-hydroxyethyl)piperazine in the presence of a catalytically effective amount of aromatic carboxylic acid at a temperature of about 245°–260° C. The reaction was carried out in the presence of an aromatic compound having an atmospheric boiling point of 496° F sold under the trade name DOWTHERM A by the Dow Chemical Company, Midland, Mich. 48640, which was used as a solvent in a suitable closed stirred reaction vessel equipped with a distillation column which served to keep the unreacted N-(2-hydroxyethyl)piperazine and solvent from leaving the reaction zone. Effluent vapors from the reaction vessel and distillation column were passed through a condenser and water was added. The crude aqueous triethylenediamine reaction mixture was collected and analyzed. The crude aqueous triethylenediamine reaction product mixture analyzed as follows: 33 wt. % triethylenediamine; HEP, 0.8 wt.

%; piperazine, 0.2 wt. %; water, 65.8 wt. %; and unknown heavies, approximately 0.2 wt. %.

EXAMPLE I

A batch azeotropic distillation still was charged with 386 g propylene glycol, 75 g dipropylene glycol, 453 g cyclohexane and 595 g crude aqueous triethylenediamine reaction mixture (33 wt. % triethylenediamine prepared as described hereinabove). The mixture was then continuously heated whereby water was removed via the water-cyclohexane azeotrope. A portion of the cyclohexane was also distilled from the remaining anhydrous mixture. The azeotropic distillation was performed at atmospheric pressure and the final pot temperature was 174° C. After cooling, it was determined that 666 g of liquid remained in the azeotropic distillation still. This liquid was then transferred to a conventional batch flash distillation apparatus equipped with conventional means for condensing vapors taken overhead. The liquid was flash distilled at atmospheric pressure and two overhead cuts were collected. The first cut contained the remaining cyclohexane and was collected with termination at a head temperature of 184° C. The second cut was collected from a head temperature of 184° C to a termination head temperature of 185° C. The second cut weighed 486 g and contained 34.7 wt. % triethylenediamine dissolved in propylene glycol with the presence of a small amount of dipropylene glycol being detected. The second cut solution was clear, i.e., low in color, and essentially dry with only 0.05 wt. % water being analyzed. The residue remaining in the flash distillation pot was primarily dipropylene glycol which had been initially charged to provide a heel at the end of the flash distillation. The flash distillation was carried out with no triethylenediamine freezing problems being observed in the condenser.

EXAMPLE II

In this example dipropylene glycol was used as a solvent to show a contrast to Example I.

A mixture of 461 g dipropylene glycol, 453 g. cyclohexane and 595 g crude aqueous triethylendiamine reaction product mixture (33 wt. % triethylenediamine) was dried by azeotropic distillation employing the azeotropic distillation still apparatus and procedures described in Example I. The liquid residue remaining in the azeotropic still pot weighed 713 g and was charged to the batch flash distillation apparatus also described in Example I. The liquid was then distilled taking a first cut overhead which contained the remaining cyclohexane and was collected at a final head temperature of 184° C. Distillation was continued taking a second cut at a head temperature of above 184° C to 222° C. However, considerable freezing of triethylenediamine in the condenser system was observed during the taking of the second cut. The distillation unit operated only with great difficulty due to the condenser plugging observed. The difficulties were in direct contrast with the smooth operation observed in Example I, wherein propylene glycol was employed.

EXAMPLE III

To a conventional batch distillation still equipped with a reflux condenser was charged 461 g propylene glycol and 595 g crude aqueous triethylenediamine reaction product mixture (33 wt. % triethylenediamine). The admixture was then distilled at atmospheric pressure with the collection of three distillation cuts. The head temperature, reflux ratio and weight of each distillation cut collected are set forth in the following Table I.

TABLE I

| Cut No. | Head Temp., °C | Reflux Ratio | Weight, g | Description |
| --- | --- | --- | --- | --- |
| 1 | IBP to 121 | 5/5 | 388 | Water cut |
| 2 | 121 to 185 | 20/5 | 68 | Intermediate cut |
| 3 | 185 to 187 | 5/5 | 489 | Product Cut |

Cut No. 1 consisted essentially of water while Cut No. 2 consisted of triethylenediamine, propylene glycol, water and a substantial amount of the piperazine present in the initial charge. Cut No. 3, the product cut, was a clear, light colored liquid containing 0.36 wt. % water and 29 wt. % triethylenediamine, the remainder being propylene glycol with very minor amounts of piperazine present. The distillation was carried out in a straight forward manner with no signs of triethylenediamine freezing being observed at any step of the process.

Obviously, many modifications and variations of the invention as hereinbefore set forth may be made without departing from the spirit and scope thereof, and, therefore, only such limitations should be imposed as are indicated in the appended claims.

What is claimed is:

1. Improved process for directly recovering a substantially pure triethylenediamine solute in liquid propylene glycol solution from a crude triethylenediamine reaction product mixture obtained from a liquid phase process for the preparation of triethylenediamine comprising the steps of:

admixing propylene glycol with said crude triethylenediamine reaction product mixture to form a crude triethylenediamine reaction product-propylene glycol admixture;

distilling said admixture under conditions such that said triethylenediamine and said propylene glycol codistill; and collecting the resultant codistillate as the substantially pure triethylenediamine solute in liquid propylene glycol solution.

2. The process of claim 1 wherein said collecting of the resultant codistillate is accomplished at a head temperature of from about 185° to about 195° C at atmospheric pressure.

3. The process of claim 1 wherein said propylene glycol is present in said reaction product admixture in an amount sufficient to provide a collected codistillate of triethylenediamine and propylene glycol containing from about 33 weight percent to about 37 weight percent triethylenediamine.

4. The process of claim 1 wherein said crude triethylene reaction product mixture contains from 45 to 55 wt. % water.

5. The process of claim 1 wherein said crude triethylenediamine reaction product mixture is obtained by heating N-(2-hydroxyethyl)piperazine in the presence of a carboxylic acid catalyst to temperatures of from about 230° to 350° C, and collecting the vaporous effluent therefrom.

6. An improved process for preparing substantially pure liquid solutions of triethylenediamine and propylene glycol comprising the steps of:

initially forming a crude triethylenediamine reaction product mixture by heating N-(2-hydroxyethyl)-piperazine in the presence of an aromatic carboxylic acid and a hydrocarbon solvent having a boiling point of about 250° C to temperatures of from about 245° to 260° C, and collecting the vaporous effluent therefrom;

admixing from about 45 to 55 wt. % water with said crude triethylenediamine reaction product mixture to form a crude aqueous triethylenediamine reaction product mixture;

admixing propylene glycol with said aqueous reaction product mixture to form a crude aqueous triethylenediamine reaction product-propylene glycol admixture;

distilling said admixture under conditions such that said triethylenediamine and said propylene glycol codistill; and collecting the resultant codistillate at head temperatures of from about 185° C to about 195° C at atmospheric pressure as the substantially pure liquid solution of triethylenediamine and propylene glycol.

7. The process of claim 6 wherein said propylene glycol is initially admixed with said aqueous phase in an amount sufficient to provide a collected codistillate solution of triethylenediamine and propylene glycol containing from about 33 weight percent to about 37 weight percent triethylenediamine.

8. An improved process for directly recovering an essentially pure triethylenediamine solute in liquid propylene glycol solution from a crude triethylenediamine reaction product mixture obtained by heating N-(2-hydroxyethyl)piperazine in the presence of a carboxylic acid catalyst to temperatures of from about 230° to 350° C, and collecting the vaporous effluent therefrom, comprising the steps of:

admixing propylene glycol with said crude triethylenediamine reaction product mixture to form a crude triethylenediamine reaction product-propylene glycol admixture;

distilling said admixture under conditions such that said triethylenediamine and said propylene glycol codistill; and collecting the resultant codistillate as a substantially pure triethylenediamine solute in a liquid propylene glycol solution.

9. An improved process for directly recovering a substantially pure triethylenediamine solute in liquid propylene glycol solution from a crude triethylenediamine reaction product which is substantially free of by-products which have the same boiling point as that of a triethylenediamine propylene glycol codistillate comprising the steps of:

admixing propylene glycol with said crude triethylenediamine reaction product mixture to form a crude diethylenetriamine reaction product propylene glycol admixture;

distilling said admixture under conditions such that triethylenediamine and said propylene glycol codistill; and, collecting the resultant codistillate as a substantially pure triethylenediamine solute in liquid propylene glycol solution.

10. The process of claim 9 wherein said collecting of the resultant codistillate is accomplished at a head temperature of from about 185° to about 195° C at atmospheric pressure.

11. The process of claim 9 wherein said propylene glycol is present in said reaction product admixture in an amount sufficient to provide a collected codistillate of triethylenediamine and propylene glycol containing from about 33 wt. % to about 37 wt. % triethylenediamine.

12. The process of claim 9 wherein said crude triethylenediamine reaction product mixture contains from 45 to 55 wt. % water.

* * * * *